United States Patent [19]

Saxena

[11] 4,016,250
[45] Apr. 5, 1977

[54] METHOD FOR TESTING FOR PREGNANCY
[75] Inventor: Brij B. Saxena, Englewood, N.J.
[73] Assignee: Cornell Research Foundation, Inc., Ithaca, N.Y.
[22] Filed: Nov. 11, 1974
[21] Appl. No.: 522,760

Related U.S. Application Data

[63] Continuation-in-part of Ser. No. 454,145, March 22, 1974, abandoned.
[52] U.S. Cl. .............................. 424/1; 23/230 B; 23/230.3; 424/1.5; 424/12; 260/112 R
[51] Int. Cl.$^2$ ...................................... G01N 33/16
[58] Field of Search ............. 23/230 B; 424/12, 1.5, 424/1

[56]  References Cited
OTHER PUBLICATIONS

F. Haour et al., J. Biol. Chem., 249(7), 2195–2205 (1974).
K. M. J. Menon et al., Biochem. and Biophys. Res. Comm., 56(2) (1974).
Ch. V. Rao et al., Biochimica et Biophysica Acta, 313, 372–389 (1973).
D. S. Skelley et al., Clin. Chem., 19(2) (1973).

Primary Examiner—Morris O. Wolk
Assistant Examiner—Sidney Marantz
Attorney, Agent, or Firm—Lawrence E. Laubscher; Ralph R. Barnard; Theodore C. Wood

[57] ABSTRACT

Method for the determination of the hormone human chorionic gonadotropin (HCG), luteinizing hormone (LH), prolactin (PRL) and HCG-like material in an aqueous sample comprising contacting a highly specific receptor for these hormones with an aqueous sample to be tested, providing a means of indicating whether binding has taken place between the receptor and hormone possibly contained in the sample and observing the indicating means to determine the presence of the hormone in the sample. PRL may be determined separately or simultaneously with the HCG and LH. The receptor is a plasma membrane extract from the corpus luteum of an animal which possesses the receptor for HCG, LH, PRL and HCG-like material. Radioassay indicating means are preferred, according to which competitive protein binding between radioisotopically labeled hormone and hormone present in the sample is radiologically determined. The method has particular application to the determination to pregnancy in the human female.

44 Claims, 4 Drawing Figures

METHOD FOR TESTING FOR PREGNANCY

CROSS REFERENCE TO RELATED APPLICATION

This application is a continuation-in-part of application Ser. No. 454,145 filed Mar. 2, 1974, now abandoned.

BACKGROUND OF THE INVENTION

The present invention relates to a method and means for the determination of the hormones human chlorionic gonadotropin (HCG), luteinizing hormone (LH) and prolactin (PRL) and more especially to a fundamentally new method and means for detection of pregnancy in the human female.

Tests for the detection of pregnancy are generally based on the determination of hormones which are produced by the developing placenta, such as gonadotropic hormones similar to those produced by the anterior pituitary gland and steroid hormones similar to those of the ovary and adrenal gland. Pregnancy tests in use today are nearly exclusively based upon an assay for the placental hormone, human chorionic gonadotropin (HCG). This hormone is found in body fluids (blood serum and urine) only during pregnancy, with the exception of several other very rare hormone-producing conditions of the body. The International Unit (I.U.) of HCG was adopted in 1938 and is defined as the specific gonadotropic activity of 0.1 mg. of a dried standard kept at the National Institutes of Health, London, England.

The earliest tests for pregnancy were based upon biological in vivo methods for determining the presence of HCG. For example, the earliest test, the Aschheim-Zondek test was based upon the ability of HCG injected subcutaneously in mice to produce corpora lutea. The Friedman test is another biological test in which a urine sample of the suspected pregnancy is injected into the ear vein of a mature female rabbit which has been isolated 3 to 4 weeks, and 48 hours after injection the ovaries are examined for ruptured hemorrhagicfollicles, which indicate a positive reaction. A lesser known test developed by Kupperman in 1943 involves the injection of the patient's urine into a female rat with subsequent inspection of the ovary for signs of hyperemia. While the two hours necessary for conducting this test is considerably shorter than the 48 hours required for the Friedman test and the nearly five days required for the Aschheim-Zondek test, this test is not as reliable since it requires a skilled technician to differentiate a slightly pink negative ovary from a reddened positive ovary to attain a high degree of accuracy. A test developed by Galli and Mainini in the late 1940's also requires only approximately two hours to conduct the test; however, this test involves the injection of the patient's urine into frogs with the subsequent observation for ejection of sperms, and these animals are relatively insensitive compared with rabbits, mice and rats.

All of the foregoing biological test suffer from serious disadvantages, including the availability of animals, the need to maintain a large colony of animals, and relatively long periods of testing, frequent yielding of false positive and negative results, and most significantly, the fact that a positive test can be achieved with only a 95% degree of reliability only after a period of 25 to 30 days following ovulation.

A second generation of pregnancy tests developed during the early 1960's are characterized as immunological or immunochemical procedures. Since HCG is a protein hormone, it acts antigenically in a heterologous species. Accordingly, when HCG is injected by suitable techniques into an appropriate test animal, most typically a rabbit, an antibody to HCG is produced within the animal. In early tests utilizing this principle, it was attempted to utilize the antigen-antibody direct precipitin reaction, according to which a visible precipitate would form as a result of the combination of HCG and its antibody, to detect the presence of this hormone. More common procedures involved so-called indirect methods of determination, such as the latex particle slide test of Brody and Carlstrom and hemagglutination and inhibition test of Wide and Gemzel. In the former procedure, an antiserum is added to the urine of a patient followed by a latex carrier which has been coated with HCG. If the urine specimen is of a pregnant woman and contains HCG, the antibodies in the antiserum will be neutralized and will not therefore react with the HCG coated on the carrier to produce agglutination. In the latter testing method, a similar principle is employed except that the indicator comprises HCG conjugated with red blood cells or formalinized red blood cells. The first test may be carried out in a period of only about two minutes whereas the second requires approximately two hours. Either the patient's urine or blood may be employed for these test procedures.

In a very recently developed pregnancy testing procedure based upon a modification of the basic immunological mechanism, radiological means are employed to detect and/or measure the presence of HCG in the patient's blood (or urine). See, for example, Goldstein et al. in Fert. Steril., Vol. 23, page 817 (1972). In these radioimmunoassay tests, the antibody is placed in contact with a mixture of the patient's body fluid to be tested and a known amount of HCG tagged with a radioactive isotope, and the HCG in the test sample and the labeled HCG compete for interaction with the HCG antibody. The antibody is then separated from the fluid and either fraction may be analyzed radiologically to determine the respective proportions of the labeled and unlabeled HCG which became bound to the antibodies, and the concentration of HCG in the sample can be calculated from this information since the proportion of labeled and unlabeled HCG will be in the same proportion in both fractions. The radioimmunoassay techniques have overcome one significant limitation of the immunochemical pregnancy test, namely, that of sensitivity. Radioimmunoassay techniques are several thousand times more sensitive than the above-described indirect tests, and accordingly, permit a detection of pregnancy much earlier than the 25 to 30 days following ovulation required with the latex particle slide test and the hemagglutination test. However, even though pregnancy may be detected after the 10th or 12th day following ovulation with a 95% degree of reliability by the radioimmunoassay method, these tests have the disadvantage that they require more time to carry out, typically about 24–48 hours.

The most serious drawback, however, with all previously known pregnancy testing techniques involves the frequent indication of false positive and negative results. In the case of the immunochemical pregnancy test, this difficulty is due to non-specific immune response related to non-specific antibody-antigen reactions. For example, the presence of a common hormone, non-specific alpha-subunit among follicle stimulating hormone (FSH), luteinizing hormone (LH), HCG and thyroid stimulating hormone (TSH), and homologies in the amino acid sequence of the hormone-specific beta-subunits have caused further difficulties in producing specific antisera for use in the immunochemical techniques. These difficulties are exaggerated in radioimmunoassay methods due to the high degree of sensitivity of this technique. This last-mentioned drawback has been partially circumvented by producing antisera specific to the beta-subunit of HCG; however, this manipulation requires the use of valuable material, immunization, selection and purification to achieve specific antibodies, which procedures are time consuming, expensive and very cumbersome. In spite of these precautions, the goal of near 100% reliability in the detection of pregnancy by radioimmunoassay has not been accomplished.

Furthermore, a serious need exists for a means to detect ectopic pregnancies at the earliest possible moment. Such pregnancies have negative hemagglutination or latex slide tests in 40 to 60% of all patients, even after the 25-30 day period following ovulation required to perform these tests. The reason for this relates to the belief that the immunochemical pregnancy testing techniques provide for detection of a pregnancy only after implantation of the fertilized ovum has occurred. As described hereinabove, all of the heretofore known pregnancy testing methods suffer from this disadvantage in that they are not effective until after nidation. A test which could determine the presence of a pregnancy during the period between fertilization of the ovum and implantation of the fertilized ovum would be invaluable in the treatment of, for example, threatened abortion in women who habitually abort, cases involving artificial insemination and in connection with new contraceptive methods which effectively terminate a pregnancy prior to implantation.

The presence of specific receptors for the various hormones has long been suspected in target cases of both humans and animals, and researchers have had success within the last half decade in identifying and directly studying certain of these receptors and their interaction with many respective hormones. Preliminary studies undertaken by the present inventor have suggested the presence of a receptor for HCG in the corpus luteum of pregnant or pseudo-pregnant rats. Gonadotropins, Chapter 21, 1972, John Wiley & Sons. These preliminary studies, however, gave no indication of whether a similar receptor is present in humans or other animals, whether the receptor found in rats is species specific or specific even for HCG, whether it would be a reliable indicator for HCG in body fluid samples or whether it is stable over any extended period of time.

Prolactin (PRL) represents a hormone which for many years was not believed to be present in humans. Its presence in humans was confirmed in the early 1970's. The presence of PRL receptors in mammary tissue has been documented, and the hormone is believed to play a role in breast cancer, pituitary tumors, lactation disorders, hypothyroidism and other disorders. There are thought to be as many as 84 different functions of PRL involving complex interaction with other pituitary gonadal and adrenal hormones, possibly in the role as an intermediary regulator for these other hormones. A luteotropic as well as a luteolytic role of PRL during the estres cycle of the rat has also been suggested, and there is some evidence developed in the last few years regarding studies of the rat. The specific binding of PRL to rat ovary has been suggested very recently in the literature, but no specific receptor has been identified. Turkington et al., Rec. Prog. Horm. Res., 29:417 (1973). Studies by several investigators have suggested that PRL has little function in the maintenance of corpus luteum in humans. Hwang et al., Proc. Nat. Acad. Sci., 68:1902 (1971); Midgley et al., Proc. IV Int. Cong. Endocrinal, Int. Cong. Series No. 273, Excerpta Medica, Amsterdam, 1972.

In view of the maladies identified above which are known to involve the hormone PRL, it is desired oftentimes to determine and/or monitor the PRL content in a test sample obtained from a subject, for example, a sample of body fluid. In some cases, only small samples are available, e.g., pediatric cases, and therefore, it is desired to have a very specific test which requires only a small sample and only a short period of time to carry out. Specificity is desired in order to differentiate from other hormone species which may be present in the sample, and this is particularly true in cases where it might be desired simultaneously determine or measure two or more different hormones. There exists at present no truly specific means for making such a determination.

SUMMARY OF THE INVENTION

It is therefore an object of the present invention to provide a method for the determination of human chorionic gonadotropin (HCG), luteinizing hormone (LH), prolactin (PRL) and HCG-like materials in an aqueous sample.

Another object of the present invention resides in the provision of a pregnancy testing method which produces nearly 100% reliability in detecting pregnancy.

It is also an object of the present invention to provide a method for the detection of ectopic pregnancy and threatened abortion wherein the pregnant condition may be ascertained 6 to 8 days following inception.

A further object of the present invention resides in providing a pregnancy detection method according to which a pregnancy can be detected as early as the sixth to eighth day following ovulation with almost one hundred percent reliability.

It is additionally an object of the present invention to provide a means for determining the presence of the hormone HCG in an aqueous sample, particularly for the purpose of recognizing pregnancy in the human female by investigating a sample of body fluid.

Another object of the invention resides in the provision of a method for measuring the content of PRL in an aqueous sample, especially in a sample of body fluid.

It is also an object of the invention to provide a method and means for simultaneously determining HCG, or LH and PRL in an aqueous sample, particularly a very small sample of body fluid.

A further object of the present invention resides in providing the particular receptor employed in the radioreceptorassay method set forth above.

It is also an object of the present invention to provide a method for producing the specific receptor employed in the radioreceptorassay method referred to above.

In accomplishing the foregoing objects, there has been provided in accordance with the present invention a method for the determination of human chorionic gonadotropin (HCG), luteinizing hormone (LH) and HCG-like material and/or prolactin (PRL) in an aqueous sample involving the steps of contacting such a sample with an agent capable of selectively binding the hormone, providing a means of indicating whether such binding has taken place and observing the indicating means to determine the presence of the hormone in the sample, wherein a particularly improved aspect comprises the binding agent being a plasma membrane extract from the corpus luteum of an animal which possesses the receptor for the hormone HCG and/or PRL. The indicator system employed in this method may be any of those conventionally employed in a similar immunochemical method for determining proteins and/or polypeptides. For example, the indicator may be a material which has been treated with the hormone so that in the presence of the instant receptor, the indicator will discolor, become colored, agglutinate, precipitate or give some other visible indication (for example, fluoresence) of the presence or absence of the hormone in the fluid being tested, or preferably, the more accurate radiological measuring techniques may be employed. In applying this method for the detection of pregnancy in human females, a blood or urine sample is contacted with the above-described specific receptor and the presence or absence of HCG in the sample is determined based upon the amount of binding evidenced by the indicator system.

In a preferred embodiment of the present invention, there is provided a method for the determination of HCG in an aqueous sample, preferably the blood serum or urine of a patient having a suspected pregnancy, comprising contacting a highly specific receptor for the hormone HCG, which receptor is a plasma membrane extract from the corpus luteum of an animal possessing the receptor for this hormone, with the aqueous sample having added thereto an amount of HCG which has been labeled with a radioactive isotope. In this method, the possible HCG present in the sample and part of the radioactively labeled HCG are bound to the receptor. The receptor with its bound HCG is then separated from the aqueous sample and the radioactivity of one or both of the separated fractions is measured to determine the concentration of HCG in the aqueous sample, this concentration being a function of the measured radioactivity. It is preferred to obtain the receptor from the corpus luteum of a cow, sheep, horse or hog, particularly from an animal which is pregnant, and most preferably an animal during the first trimester of pregnancy.

A further embodiment comprises a method for determining the hormone prolactin (PRL) in an aqueous sample, again preferably a body fluid, including the steps of contacting the sample with a highly specific receptor for PRL, this receptor also being a plasma membrane extract of the corpus luteum of an animal possessing this receptor, and providing in the sample an amount of PRL labeled with a radioactive isotope. The remaining steps are identical to those set forth above for determining HCG. This method can be used as an indication of pregnancy in a human female or for indicating other disorders involving the presence of prolactin.

There is also provided in accordance with the invention a method for simultaneously determining two or more different hormones contained in a single aqueous sample. In this embodiment, the steps are similar to those for measuring single hormones, except that the aqueous sample is contacted with one or more agents capable of selectively binding each of the hormones to be determined, providing a separate and distinguishable means for indicating whether binding has taken place for each hormone and observing each of the indicators to determine the presence of each hormone. The binding agent is a plasma membrane extract from a body organ of a species which is known to possess in the organ a specific receptor for each of the hormones to be measured. Preferably the receptor is a plasma membrane extract of the corpus luteum of a mammal, which possesses receptor sites for both HCG and PRL. The preferred indicating means comprise different radioactive isotopes, for example, different isotopes of iodine such as $^{125}I$, $^{131}I$, $^3H$ and $^{14}C$. With such an indicator, HCG and PRL can be simultaneously measured by contacting the receptor with the sample and differently labeled HCG and PRL, so that part of the labeled and unlabeled hormones are bound to the receptor, separating the bound and unbound hormone from the sample and counting the radioactivity of each isotope species to determine the presence of the respective hormones in proportion to the radioactivity measured.

In another embodiment of the present invention, there is provided a reagent for receptor-chemical determination of the hormone HCG, which reagent comprises in substantially pure form the specific fraction of plasma membrane extract from the corpus luteum of an animal possessing the receptor for HCG, the specific fraction being one which is capable of selectively binding biologically active human chorionic gonadotropin.

In yet another embodiment of the present invention, there is provided a method for the preparation of a reagent for receptor-chemical determination of the hormone HCG, comprising the steps of preparing a finely comminuted tissue homogenate from corpus luteum tissue of an animal which possesses the receptor for HCG, separating the plasma membranes from said homogenate and selecting the plasma membrane fraction capable of selectively binding biologically active human chorionic gonadotropin.

The subject testing procedure is also suitable for detecting pregnancy in animals. Accordingly, it may be used to detect pregnancy in any of the animal species wherein the specific receptor of the invention is found, i.e., mammals and possibly selected non-mammals.

A further embodiment of the invention comprises means for the determination of human chorionic gonadotropin (HCG), luteinizing hormone (LH) or HCG-like material in an aqueous sample, comprising (a) a first reagent and a second reagent; (b) said first reagent comprising in substantially pure form the specific fraction of plasma membrane extract from the corpus luteum of a species having the receptor for human chorionic gonadotropin capable of selectively binding biologically active human chorionic gonadotropin; (c) said second reagent comprising labeled human chorionic gonadotropin capable of emitting radiation, said first reagent being intended to be contacted with the sample containing the hormone to be measured and with the second reagent to bind part of the labeled and unlabeled hormone to said receptor; (d) means for measuring the amount of labeled hormone bound to said receptor, the emitted radiation therefrom being a function of the concentration of the hormone in the aqueous sample. This embodiment preferably takes the form of a pregnancy testing kit.

Also provided according to the invention is a means for the determination of prolactin (PRL) in an aqueous sample, comprising (a) a first reagent and a second reagent; (b) said first reagent comprising in substantially pure form the specific fraction of plasma membrane extract from the corpus luteum of a species having the receptor for prolactin capable of selectively binding biologically active prolactin; (c) said second reagent comprising labeled prolactin capable of emitting radiation, said first reagent being intended to be contacted with the sample containing the hormone to be measured and with the second reagent to bind part of the labeled and unlabeled hormone to said receptor; (d) means for measuring the amount of labeled hormone bound to said receptor, the emitted radiation therefrom being a function of the concentration of the hormone in the aqueous sample.

Finally, in another embodiment of the invention there is provided a means for the determination of a plurality of hormones in an aqueous sample, comprising (a) a first reagent and a number of second reagents equal to the number of hormones to be determined; (b) said first reagent comprising a substantially pure form the specific fraction of plasma membrane extract from a body organ of a species having the specific receptor in said organ for selectively binding each of said hormones in biologically active form; (c) said second reagents comprising each of said hormones to be determined in a labeled form capable of emitting radiation, said emitted radiation being different for each labeled hormone, said first reagent being intended to be contacted with the sample containing the hormone to be measured and with the second reagents to bind part of the labeled and unlabeled hormones to said receptor; (d) means for measuring the amount of labeled hormones bound to said receptor, the emitted radiation from each labeled hormone being a function of the concentration of the respective hormone in the aqueous sample. In this embodiment, the first reagent is preferably the plasma membrane extract of a mammal and the second reagents comprise HCG and PRL labeled with different isotopes.

Further objects, features and advantages of the present invention will become apparent from the detailed description of the invention which follows, when considered with the attached drawing.

DETAILED DESCRIPTION OF THE INVENTION

Figure 1:
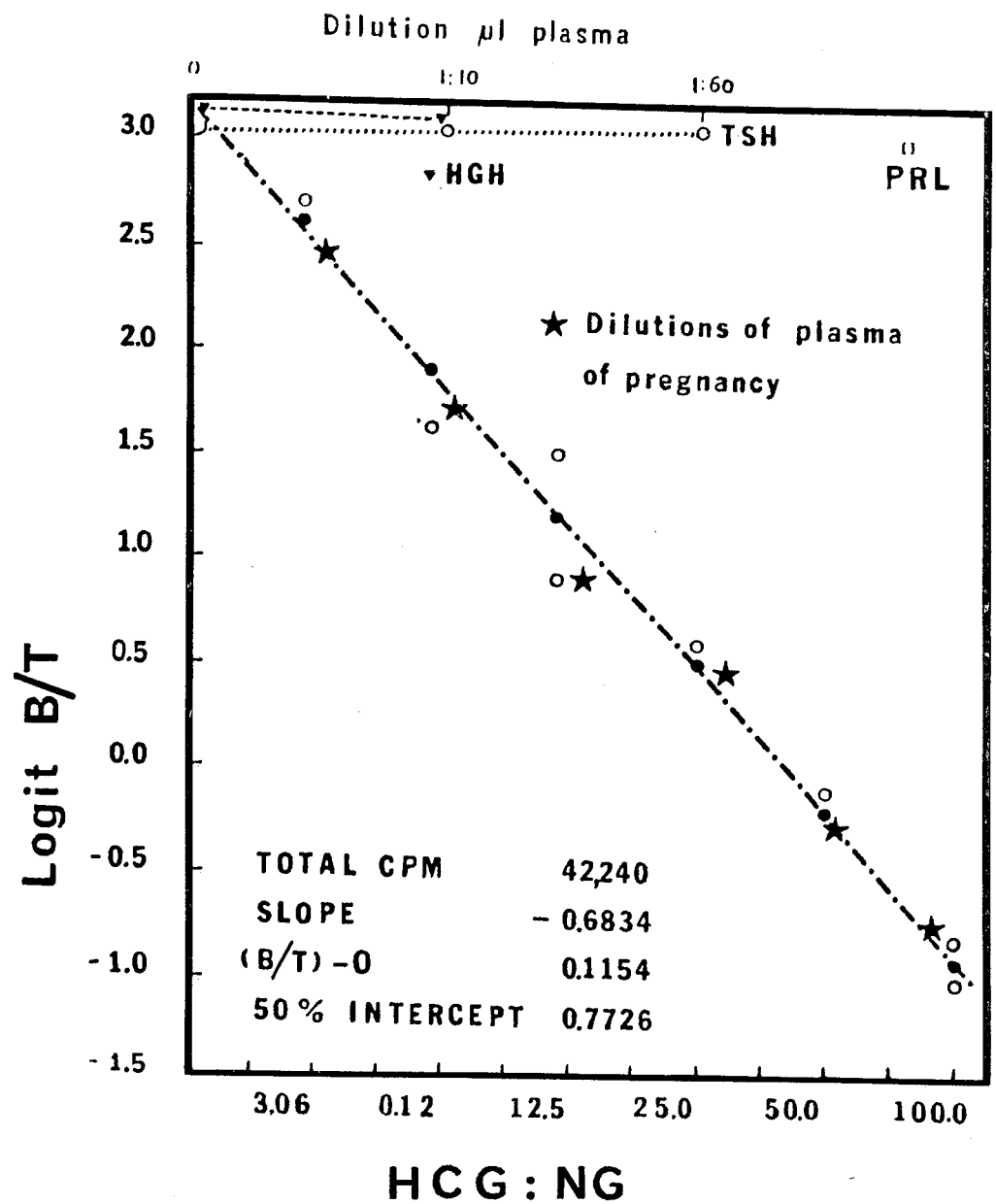
FIG. 1 is a logit-log linearization of the competitive inhibition response of the radioreceptorassay of HCG, serving as a calculation standard for the method of the present invention.

In accordance with the present invention, there has been discovered a novel and very specific method for determination of the hormone human chorionic gonadotropin (HCG) and/or prolactin (PRL). In contradistinction to previous biological tests for HCG which have proved to be very impractical and to more recently developed immunochemical tests which are based upon the principle of antigen-antibody binding but which are not sufficiently reliable, the present method is based upon the use of a highly selective receptor for HCG. The receptor is isolated from the target tissue of an appropriate animal, whereas in the case of immunochemical methods, an antiserum is produced from the blood of a suitable animal which has been injected with the hormone to produce antigen-antibody response.

Prior to the present invention there has been no acknowledged reason for determing PRL in humans, and hence, no emphasis on devising suitable precedures. The invention is based upon discovery of a specific receptor for this hormone. The use of a specific receptor isolated from the target tissue of an animal which possesses this specific receptor overcomes, apparently entirely, the drawback of non-specific responses which often occur in conjunction with immunochemical procedures. In most cases the specific receptor binding requires the natural configuration of a hormone in its biologically active form. Accordingly, when the receptor-chemical testing procedure is combined with radio-assay indicating techniques, there results a radioreceptorassay method which possesses the degree of sensitivity of the radioimmunoassay techniques and at the same time the degree of specificity of bioassay, and therefore, this method evidences greater sustained accuracy over all existing immunological and biological hormone tests, particularly tests for pregnancy.

Furthermore, because the receptor requires the biologically active form of the hormone for binding, the endogenous synthesis of a metabolically defective HCG, which normally would give a positive reaction in accordance with the immunochemical testing procedures but which is assumed to be incapable of sustaining pregnancy, would not give rise to a false positive test in accordance with the testing method of the present invention.

As pointed out in the introduction, the hormone prolactin has been suggested as having some function in the estres cycle of the rat, but at the same time has not been identified as having any role in the ovarian or reproductive processes of humans. As a basis for this invention, it has been discovered that there is an increase in the level of PRL in the female during pregnancy. Furthermore, it has been discovered that ovarian tissue from several species, including the cow and humans, contains specific receptor sites for the hormone PRL, in addition to receptor sites for HCG.

Thus, in addition to providing a generally applicable procedure for determining PRL in connection with the various maladies mentioned above, it is also possible to employ the method of the invention for determining, or preferably aiding in the determination of pregnancy. A detected increase in the PRL level in a woman suspected of being pregnant gives a further indication, together with the determination of HCG in accordance with the invention, that pregnancy in fact exists. This added degree of confirmation is of great value, particularly, in cases involving abnormal pregnancy or threatened abortion. It is believed that PRL plays an important role in fetal development, and accordingly, its determination provides further information to that obtained by a determination of HCG.

In a preferred aspect of the present invention, it is possible to simultaneously determine both HCG and PRL, since it has been found that the same receptor possesses receptor sites for both of these hormones. This is a particularly unexpected discovery in view of the fact that receptor sites for PRL have not heretofore been confirmed in the corpus luteum of any animal and receptor sites for HCG have been shown only in the rat. Simultaneous detection has obvious advantages in pregnancy testing in view of the above-indicated role of PRL in pregnancy. A single body fluid sample and a single testing procedure provide the most complete and most accurate indication of pregnancy available.

This simultaneous determination technique is not limited to the hormones HCG and PRL. For example, it is known that mammary tissue contains receptor sites for more than one hormone, e.g., estrogen, prolactin and oxidocin, and therefore the technique of the invention is equally applicable to simultaneous determinations of these hormones using a receptor derived from breast tissue.

It has also been discovered in accordance with the present invention that the radioreceptorassay technique enables the detection of pregnancy as early as one week following ovulation. This represents indeed a significant advance in the field of pregnancy determination tests, since heretofore the pregnancy condition could not be detected earlier than about the tenth or twelfth day following ovulation. This result is more significant when it is realized that the vast majority of pregnancy tests are carried out today not by means of the radioimmunoassay procedure which permits determination as early as ten or twelve days following ovulation, but rather by means of the hemagglutination or latex slide tests, which as pointed out hereinabove permit a determination of pregnancy only after about 25 or 30 days following ovulation. Radioimmunoassay tests require at least 24 hours of laboratory time and typically about 48 hours of testing time, coupled with cumbersome and expensive procedures for preparing sufficiently specific antibody or antiserum. On the other hand, the time required to carry out the testing procedure in accordance with the present invention amounts to no more than about one hour and typically only about one-half hour. The practical advantages flowing from such a pregnancy testing method which permits determination of the pregnancy condition prior to implantation of the fertilized ovum in the endometrial tissue have been briefly discussed above, and these advantages as well as the significant benefits in terms of basic research in the field of human reproduction resulting from the present invention are readily apparent to those knowledgable in this art.

In view of the fundamental similarities in the binding mechanism of the instant receptor-chemical testing mechanism and the well-known immunochemical testing mechanism it is possible to utilize the previously developed indication mechanisms within the context of the present invention. Accordingly, the indicator system may consist of an indicator material which has been treated with HCG so that in the presence of the receptor, the indicator material will discolor, become colored, agglutinate, precipitate or give some other visible or chemical indication of the presence or absence of HCG in the aqueous sample or body fluid being tested. From the foregoing, however, it is obvious that the most effective results are obtained when a radiological assay technique is employed as the indicator system. Accordingly, the radioreceptorassay embodiment of the present invention represents clearly the most preferred embodiment. Nonetheless, it is to be understood that the present invention does not reside in the provision of a particular indication system for use in the subject method, but rather in the fundamental and novel employment of receptor-chemical techniques and a specific receptor to determine the presence of HCG and/or PRL.

In view of the extreme degree of specificity and sensitivity of the radioreceptorassay method of the present invention, it is possible to make a satisfactory determination on an extremely small sample. For example, in utilizing the method of the present invention as a test for pregnancy, it is possible to perform the test utilizing only about 0.1 ml. or less of blood taken from the patient. This withdrawal from the patient can be accomplished by means of a simple pinprick in the end of a finger. Furthermore, the method of the invention is effective to determine the presence of HCG in any aqueous sample, and accordingly, either blood serum or a urine sample from a patient may conveniently be employed.

The specific receptor employed in the testing procedure according to the present invention is derived from ovarian tissue. As pointed out hereinabove, the receptor is significantly more selective for HCG and HCG-like materials or PRL than is an HCG or PRL antibody, since the receptor requires the native configuration of the hormone in its biologically active form for binding. Hence, there is no possibility of non-specific immune response. In all animals which possess this specific receptor, it is readily detectable in the ovarian tissue which represents the target tissue of the hormone. While the receptor may be isolated from any mammal and possible from certain non-mammals, it is preferred to obtain the receptor from the ovaries of relatively large animals, such as cows, sheep, pigs, horses and the like in view of the fact that these animals have proportionately a greater amount of ovarian tissue, and furthermore, a ready supply of such tissue exists by virtue of the fact that these animals are commercially slaughtered for their meat. It has been determined that up to 200 pregnancy tests can be performed from a single cow ovary. The ovaries, for example, of rats are so small as to effectively render impractical the use of animals of this type as a source of receptor. As discussed below, the testing method of the invention is also applicable to animals which possess the receptor, and therefore, positive evaluation of pregnancy in a given species also provides a method for screening animals for the presence of the receptor.

Preferably, the animal from which the receptor is obtained is in a pregnant condition at the time of slaughter, since at this time the amount of ovarian tissue and the number of receptor sites is at a maximum. The first trimester of pregnancy has been found to be the most advantageous time for obtaining the tissue.

The specific receptor of the invention is obtained by separation of pure plasma membranes from the ovarian tissue followed by evaluation of the various plasma membrane fractions by testing against isotopically labeled HCG or PRL and selecting the fraction which shows the greatest binding for the hormone. The receptor is extremely stable and can be stored for long periods of time, or may even be reused in a second or subsequent testing procedure. The plasma membrane receptor is stable after lyophilization for pregnancy test. The exact procedure for obtaining the receptor is described more fully below.

Since the testing procedure of the invention is not species specific, it may also be utilized to detect pregnancy in any of the animals which have been found to possess the specific receptor of the invention. Thus, even though the receptor is very specific for HCG in humans and LH in humans and animals, it is also capable of selectively binding HCG-like proteins which play in animals a role corresponding to HCG in humans, i.e., they correspond to the chorionic gonadotropins in humans. The same holds true for PRL. The advantage to this is that standard laboratory test animals, such as monkeys, dogs, rabbits, mice, etc., can be tested by this method whereas separate antibodies were required for each animal in accordance with immunochemical testing procedures.

Labeling of the HCG or PRL with a radioactive isotope can be effected in the conventional manner, with a suitable isotope for this purpose being selected, for example, from $I^{131}$, $C^{14}$, $H^3$ and the like. A particularly suitable isotope is a radioactive isotope of iodine such as $I^{125}$ in view of the fact that labeling with this isotope is relatively simple and many laboratories possess the equipment necessary to measure this isotope.

In the case of simultaneous hormone determination by the receptor assay technique of the invention, it is necessary to label each hormone to be determined with a distinguishable isotope, in order that measurement of the bound and/or unbound hormone fractions will provide a separate indication for each hormone to be determined. For example, when conducting a simultaneous determination of HCG and PRL, purified samples of these two hormones can be labeled with $^{125}I$ and $^{131}I$, respectively, and readily available counting devices can then be used to separately count each isotope.

In order to more completely describe the present invention, there are presented below several specific methods for preparing the test reagents and application of the radioreceptorassay as well as specific examples of clinical determinations utilizing the present invention, it being understood that the specific procedures are intended merely to be illustrative and in no sense limitative.

I. Radioisotopic Labeling of Hormone

Highly purified HCG (containing 12,000 I.U./mg. was utilized for the testing. The HCG was labeled with $I^{125}$ by using lactoperoxidase prepared from milk (RZ = 0.78; Sigma Company, St. Louis, Missouri). Two mCi of $I^{125}$ in 20 ul. of 0.1 M. sodium acetate buffer of pH. 60 were mixed with 25 ug. of HCG in a reaction vial. An aliquot of 50 ng. lactoperoxidase in 20 ul. and 200 ng. of $H_2O_2$ in 10 ul. of water are then added to the vial. Three aliquots of 100 ng. of $H_2O_2$ were added at five minute intervals. The end of 20 minutes, the reaction was stopped by the addition of 0.5 ml. of 0.15 M. NaCl containing 1% of bovine serum albumin (BSA) of pH. 7.0. The labeled hormone was then separated from free iodine by gel filtration on a 1x30 cm. column of Sephadex G-100 equilibriated with 0.15 m. NaCl containing 1% of BSA, pH. 7.0. The specific activity of the labeled HCG was determined by precipitation with trichloroacetic acid. Five ul. of the crude reaction mixture was diluted to 5 ml. with 0.05 M. phosphate buffer of pH. 7.5 containing 0.1% BSA. To a 200 ul. aliquot of this solution were added 400 ul. of trichloroacetic acid to a final concentration of 10% trichloracetic acid. The precipitated proteins were recovered by centrifugation. The radioactivity associated with the precipitable material was considered as protein bound and was used in the calculation of the specific activity of the labeled hormone. The crude reaction mixture was purified by gel filtration through a 1×30 cm. column of Sephadex G-50 equilbrated with 1% BSA in 0.9% NaCl. The specific activity of the HCG used in the radioreceptorassay was 20–30 uCi/ug. The biological activity of the labeled HCG used in the test, as determined by ovarian ascorbic acid depletion assay, was 8,923 I.U./mg. with 95% confidence limits of 5,826–12,250 I.U./mg.

HPRL was iodinated by the method of Hunter and Greenwood with minor modifications: To 50 ul of 0.5 m phosphate buffer, pH 7.5 were added 1 mCi of Na $^{125}I$ (New England Nuclear, Boston Massachusetts), 5 ug hPRL, and 70 ug of chloramine-T, followed after 15 second by sodium metabisulfite. One hundred mg of iobeads (Hycel Reagents, Houston, Texas) were added to the crude iodinated mixture to adsorb unreacted $^{125}I$. hPRL was also iodinated enzymatically by lactoperoxidase (Sigma Chemical Company, St. Louis, Missouri). Purification was achiefed by gel filtration on a Sephadex G-100 column (0.7 × 18 cm). The specific activity and purity of the labeled PRL were determined by chromatoelectrophoresis. $^{125}I$-hPRL capable of binding specifically to mammary tissue from lactating rat was used for the binary studies with partially purified ovarian homogenate.

II. Preparation of Receptor

All procedures in the preparation of plasma membranes were carried out in an ice bath or at 4° C. Fresh bovine ovaries from early pregnancy (first trimester: fetus length from crown to rump up to 22 cm.) were obtained from the slaughter house and stored in liquid nitrogen until processed. In a typical experiment, 100 g. of tissue from approximately 25 large corpora lutea were cut into small pieces with a sharp steel blade and ground in 500 ml. of 10 mM. Tris-HCl buffer of pH. 7.8 containing one mM. of $MgCl_2$, one MM. dithiothreitol, 10,000I.U. of Trasylol (FBA Pharmaceuticals) per liter and 0.25 M. sucrose. The homogenate was filtered through two layers of cheese cloth and the larger particles were reprocessed in 500 ml. of the buffer. The tissue was further homogenized by 10 to 15 strokes in a Teflon-glass homogenizer, Type C with clearance size of 0.12 to 0.17 mm. at 4° C. The homogenate was centifuged at 650 xg. for 20 minutes in a Sorvall refrigerated centrifuge (RC B, Rotor GSA) to remove intact cells, cell debris and nuclei. The 650 × g. supernatant was again centrifuged at 13,000 g. for 20 minutes in the same centrifuge. Supernatant was this time discarded and the pellet was resuspended in 50 to 70 ml. of the Tris-HCl buffer with the aid of the Teflon-glass homogenizer. This suspension was injected in the core of a TI-14 zonal rotor (Model Beckman Spinco L3-50) spinning at 3,000 rpm. and containing 500 ml. of a linear sucrose gradient (LKB Ultrograd 11300 pump) from 30% (w/v) to 50% (w/v) sucrose and 120 ml. of cushion of 50% (w/v) sucrose (pumping rate 20 ml./min.) An overlay of 20 ml. was injected after the sample. After two hours of centrifugation at 45,000 rpm., the centrifuge was decelerated and the rotor content displaced with 55% sucrose at 20 ml./min. The plasma membranes were displaced from the rotor in the order of increasing particle size, and fractions of 12 ml. were collected and immediately frozen until assayed for binding and enzynatic activity. Membranes were kept frozen during three months without apparent loss of binding ability. Aliquot of the fractions were taken for electron microscopy before freezing. The sucrose contained in the suspension did not interfere with the binding of the labeled HCG.

Aliquots of ovarian homogenate and suitable aliquots of the various fractions obtained from the continuous sucrose density gradient were solubilized in 1 M. NaOH containing 0.1% sodium dodecyl sulfate to determine the protein content by the method of Lowry (J. Biol. Chem., Vol. 193, page 265, 1951) using bovine serum albumin as the standard. Aliquots of the various fractions were also combined with HCG labeled with $I^{125}$ and the degree of binding measured in each case. On the basis of protein concentration, the plasma membranes containing the specific receptor for the labeled HCG showed a 10-fold greater binding than the crude ovarian homogenate.

Each fraction was also analyzed for contamination by investigating its enzymatic activity. Each fraction was assayed for 5' Nucleodiase activity by the method of Song et al. (J. Biol. Chem. Vol 262, page 694, 1967) and the inorganic phosphate liberated was measured by the method of Fiske et al. (J. Biol. Chem., Vol. 66, page 375, 1925). Cytochrome C reductase was assayed according to the method of Cooperstein et al. (J. Biol. Chem. Vol. 189, page 665, 1951).

As a further check as to purity of the plasma membranes, the individual fractions were subjected to electron microscopy. An aliquot of each protein fraction was mixed for 24 hours in 6.25% glutraraldehyde in 0.067 M. cacodylate buffer of pH. 7.3. The samples were washed for 5 minutes in chilled 0.25 M. cacodylate or phosphate buffer containing 1% $OsO_4$ of pH. 7.3 for 2 hours. Subsequently, all samples were dehydrated by passing through a graded series of alcohol and embedded in either Epon or Araldite. Sections of 0.06–0.09 um. were cut and stained in a 4% aqueous uranyl acetate solution and photographed by a Phillips Em-300 electron microscope.

A fraction showing the highest binding with the labeled HCG, a low enzyme activity and containing pure plasma membranes as shown by electron microscopy was eluted at a sucrose density of 1.16 (ca 35% w/v). Suitable aliquots of this fraction were stored in liquid nitrogen and used as the receptor.

III. Procedure of the Radioreceptorassay

The radioreceptorassay was performed in 10 × 75 ml. polystyrene tubes according to the protocol set forth in Table I.

Table I

| Sample | Diluent[1] | Plasma membrane protein: 40μg | $125_{I-HCG}$[2] |
|---|---|---|---|
| Blank | 100 μl | 100 μl | 100 μl |
| HCG[3] (ng/ml) | | | |
| 3.0 | 100 μl | 100 μl | 100 μl |
| 6.2 | 100 μl | 100 μl | 100 μl |
| 12.5 | 100 μl | 100 μl | 100 μl |
| 25.0 | 100 μl | 100 μl | 100 μl |
| 50.0 | 100 μl | 100 μl | 100 μl |
| 100.0 | 100 μl | 100 μl | 100 μl |
| Plasma (dil. 1:2 to 1:50) | 100 μl | 100 μl | 100 μl |

[1] 10 mM. Tris-HCl buffer of pH. 7.2 containing 0.1% BSA, 1 mM. $CaCl_2$ and 20 I.U. Trasylol per tube.
[2] Approximately (1.5 ng = 50,000 cpm.).
[3] 12,000 I.U. per mg. (7).

The protocol for simultaneous radioreceptorassay of hPRL and hCG is shown in Table Ia.

Table Ia

| Unlabeled Hormone[1] | | Plasma Membranes[2] | Labeled Hormone[3] | | Control Plasma[4] |
|---|---|---|---|---|---|
| hPRL | hCG | | $125_{I-hPRL}$ | $131_{I-hCG}$ | |
| 100 μl[5] | 100 μl[5] | 100 μl | 100 μl | 100 μl | 50 μl |
| 100.0 | 0.2 | | | | |
| 50.0 | 0.4 | | | | |
| 25.0 | 0.8 | | | | |
| 25.5 | 1.6 | | | | |
| 6.3 | 3.2 | | | | |
| 3.2 | 6.3 | | | | |
| 1.6 | 12.5 | | | | |
| 0.8 | 25.0 | | | | |
| 0.4 | 50.0 | | | | |
| 0.2 | 100.0 | | | | |

[1] Doubling dilution starting at 100 ng in 100 l made in incubation buffer.
[2] Approximately 100 g protein of plasma membranes isolated from pregnant cow corpora lutea.
[3] $125_{I-hPRL}$ (60–70,000 cpm/tube) and $131_{I-hCG}$ (25–30,000 cpm/tube) made in incubation buffer.
[4] Plasma from completely hypophysectomized subjects showing undetectable levels of hPRL and hLH in respective radioimmunoassays.
[5] Incubation buffer: 10 mM tris buffer, pH 7.2 containing 1 mM $MgCl_2$, $CaCl_2$, 0.1% (w/v) BSA, and 50 IU of Trasylol.

In Table I, the incubation was performed for 30 minutes at 37° C. in a Dunaboff water bath shaker. One ml. of chilled diluent was then added to each tube. The contents of the tubes were mixed on a vordex mixer and centrifuged for 20 minutes at 3,000 xg. in a refrigerated Sorvall centrifuge (Model RC2B; rotor type HS-4). The supernates were aspirated and the pellets were counted in a Packard Autogamma counter with a 51% efficiency for $I^{125}$. The standard curves and the hormonal concentration in the plasma samples were calculated by a time sharing IBM computer using logit-log transformations.

A logit-log linearization of the competitive inhibition response of the radioreceptorassay of HCG[1] is shown in FIG. 1 of drawings attached hereto. The sensitivity of the assay was less than 3.0ng/ml. with a precision of ±10%. The intra and interassay variations, as determined by assaying a plasma pool at various dilutions in twleve assays, were ±5% and ±15%, respectively, throughout the range of the assay, thus providing evidence of the high reproducibility of the assay. The plasma sample from a pregnant woman exhibited dose response identical to the HCG standard, confirming the validity of the assay. There was a complete lack of cross-reaction with highly purified preparations of FSH, PRL and HPL, as well as plasma from hypothyroid subjects, acromegalics and women during postpartum lactation, thereby indicating a high specificity of the radioreceptorassay. The radioreceptorassay did not discriminate between HCG and LH; however, a radioimmunoassay using $I^{125}$ labeled FSH, LH and HCG and antibodies to their hormone specific beta-subunits have shown that there is no rise in the plasma levels of LH and FSH during early pregnancy. Hence, lack of discrimination between HCG and LH does not effect the detection of pregnancy when utilizing the radioreceptorassay.

[1] Logit B/T represents the natural logarithon of counts bound (B) over total counts (T). For a more complete explanation of the logit B/T vs. log x linearization for radioassays, see Rodbard et al., "Statistical Quality Control of Radioimmunoassays", J. Clin. Endocrinol. Metab., Vol. 28, pp 1412–1418 (Oct. 1968).

A similar logit-log linearization plot in FIG. 4 of the drawings shows the radioreceptorassay response for HCG and samples of LH from horse, dog, rat and rabbit, all in the same system, although at different concentrations. This plot illustrates the species non-specificity of the radioreceptorassay and shows that LH in the exemplified species is similar to HCG, i.e., the lines for LH in each instance are parallel to the line for HCG.

Binding of $^{125}$I-hPRL to Ovarian Momogenate.

A reaction mixture containing 100 ul of incubation buffer containing 10 IU Trasylol (FBA Pharmaceuticals, New York, New York), 50 ul of receptor preparation equivalent to 1–300 ug of protein and 100 ul of $^{125}$I-hPRL (SA; 50–70 uCi/ug) were incubated at 37° C. for 2 hours in the absence and in the presence of 1 ug of unlabeled bovine PRL. At the end of incubation, 1 ml of ice cold buffer was added to all tubes and tubes were centrifuged at 5,000 rpm for 20 minutes. The supernatants were aspirated. The pellets containing receptor bound hormones were counted in an Automamma counter with a 51% efficiency for $^{125}$I (Packard Instrument Company, Downers Grove, Illinois). Specific binding was calculated as the difference of binding in the tubes with and without unlabeled PRL.

Specific binding of $^{125}$I-hPRL to plasma membrane from bovine corpora lutea was a saturable process. The saturation was demonstrated by incubation of plasma membrane from bovine corpora lutea (150 ug protein) at 37° C. for 2 hours in 250 ul volume with varying concentrations of $^{125}$I-hPRL. Binding capacity/mg of protein and Kd calculated by Scatchard analysis of data obtained from the saturation curve were $1.4 \times 10^{-13}$ m and Kd $= 1.4 \times 10^{-12}$.

Specific binding of $^{125}$I-hPRL to ovarian homogenates increased as a function of the amount of homogenates added and was inhibited by addition of 1 ug unlabeled bovine PRL to the incubation mixtures. Using 100 ug of homogenate, approximately 20–20% of the $^{125}$I-hPRL was bound in the absence of unlabeled PRL.

At 37° C., binding was rapid during the first 30 minutes; thereafter, binding increased slowly to reach an equilibrium at 2 hours. At 0° C., little binding was observed even after 18 hours incubation.

In order to demonstrate the specificity of $^{125}$I-hPRL binding to ovarian homogenates, human growth hormone (hGH), human follicle stimulating hormone (hFSH), human luteinizing hormone (hLH), bovine PRL (bPRL), ovine PRL (oPRL), and human chorionic somatomammotropin (hCS) were incubated at various concentrations. No displacement of $^{125}$I-hPRL bound to receptor protein was observed by hFSH and hLH. hCS and hGH were capable of displacing receptor-bound $^{125}$I-hPRL, however, the potency of hGH preparation in displacing receptor-bound $^{125}$I-hPRL was approximately 0.5–1% of hPRL. Bovine and ovine PRL preparations were shown to be essentially of similar potency in competing with $^{125}$I-hPRL. A lack of competition by FSH and LH with PRL for receptor binding demonstrates PRL specificity for the receptor sites. hCs, which has both structural and biological similarities to PRL showed some cross-reaction; however, the cross-reactivity of 0.5–1% observed with the hGH preparation is consistent with reported contamination of hGH to a very similar degree.

IV. Clinical Tests 100 subjects who were overdue for the first expected menses and were potential candidates for miniabortion had blood samples drawn for the radioreceptorassay and 24 hour urine collected for the agglutination test (Pregnosticon-Dri-Dot Test). Physical and pelvic examination, change in uterine size and consistency, and other symptoms of a possible pregnancy were evaluated. If the radioreceptorassay was positive, irrespective of a positive or negative Pregnosticon test, a miniabortion was performed. All specimens were sent to the pathological laboratory to confirm the presence of pregnancy. Three patients aborted spontaneously, and three who developed ectopic pregnancy will be discussed separately. The blood samples were centrifuged at 2,500 rpm. at 40° C. for 15 minutes, and the plasma or serum was stored at −20° C. until used.

The radiorecepetorassay for HCG in blood was performed 77 times for 72 patients to determine the presence of early gravidity. The accuracy of the test was determined by comparing it to the Pregnosticon-Dri-Dot test, the presence of gravidity was confirmed by the histopathological examination of endometrial specimens obtained at elective or spontaneous abortion. The usual clinical criteria, for example, the enlarging uterus or the onset of menstruation, provided further evidence to confirm the accuracy of the radioreceptorassay.

Forty-one patients exhibited a negative radio-receptorassay, and one false positive Pregnosticon result was associated with this group. All of the 41 subjects were confirmed as not pregnant by further clinical observations.

In 14 cases of abortion, the pathological diagnosis of the tissue extracted confirmed the result of the radioreceptorassay. Seven of the 14 miniabortions demonstrating decidual or placental tissue, which confirmed pregnancy, had a positive radioreceptorassay but negative Pregnosticon test.

The Pregnosticon test was also not sensitive enough to detect the early pregnancy, whereas the radioreceptorassay was capable of detecting a pregnacy as early as day four following ovulation and proved of great value in cases of threatened abortion. Four early threatened abortions within the first seven weeks of pregnancy demonstrated positive receptorassays, but at the same time negative Pregnosticon test. The patients aborted in each instance spontaneously, and the uterine contents were recovered revealing chorionic tissue. In the four pregnancies which terminated in spontaneous abortion, staining continued for 10 to 14 days and the uterus was not sufficiently enlarged for the duration of the gravity, suggesting an abnormality in growth and development of the embyro and placenta.

From 20 subjects visiting the fertility clinic, blood samples were drawn daily during the menstrual cycle for the determination of FSH and LH by radioimmunoassay. On the basis of BBT, plasma levels of FSH and LH, urinary excerction of estrogen and progestrone and characteristic changes in the cervical mucus as evidence of ovulation, these women were advised to become pregnant. The blood samples of four of these women who became pregnant were analyzed to establish the levels of HCG by the radioreceptorassay and the levels of FSH and LH by radioimmunoassay on the day of ovulation and during early pregnancy. The day of ovulation in these four pregnant women was subsequently confirmed by FSH and LH determination in the blood. A total of 15 normal pregnancies were tested during the period encompassing ovulation and early pregnancy. A summary of all of the subjects treated is presented in Table II.

Table II

| No. | Days following missed menses | Radioreceptor Assay blood | Agglutination Test - urine |
|---|---|---|---|
| Miniabortions | | | |
| 3 | 8 – 11 | + | + |

Table II-continued

| No. | Days following missed menses | Radioreceptor Assay blood | Agglutination Test - urine |
|---|---|---|---|
| 8 | 6 – 14 | + | – |
| 5* | 1 – 11 | – | – |
| Normal Pregnancies | | | |
| 8 | 14 – 33 | + | + |
| 7 | 0 – 42 | + | – |
| Possible Ectopics | | | |
| 1 | 14 | + | – |
| 1 | | – | – |
| Spontaneous Abortion | | | |
| 3 | 5 – 17 | + | – |
| Non-Pregnant | | | |
| 43 | 0 – 40 | – | – |
| 1 | | – | + |

*5 Non-pregnancies reported twice

The following are additional case history summaries which serve to further illustrate the value of the radioreceptorassay technique.

A 23 year old para III, gravida IV was seen eight days following the missed menstrual period. The Pregnosticon urine test was negative, and the radioreceptorassay was positive. A miniabortion performed on the following day demonstrated placental tissue.

A 20 year old nulligravida had an intrauterine device inserted, and nine months later menses were nine days late; the radioreceptorassay was positive. This assay was again positive two days later and a miniabortion revealed chorionic tissue. Two Pregnosticon tests performed on the same day were negative.

A 28 year old nulligravida with a twenty-eight day cycle was seventeen days late with the menses; the radioreceptorassay was positive and the Pregnosticon test was negative. Several days later a spontaneous abortion occurred. Three months later she was seen again five days after the first missed menstrual period. Again the radioreceptorassay was positive and the Pregnosticon test was negative. The uterus failed to grow, black staining began and persisted until a spontaneous abortion reoccurred four weeks after the missed cycle. Tissue examination of the second abortion revealed an amniotic sac without fetus.

In another instance, a 30 year old gravida I was seen twelve days after a missed cycle. At this time, the radioreceptorassay was positive and the Pregnosticon test was negative. After two weeks of irregular staining and questionable uterine enlargement, spontaneous abortion occurred.

In two patients with suspected ectopic pregnancy, one showed a positive radioreceptorassay and the other a negative test. The former was confirmed to have an unruptured tubal pregnancy. Both had negative Pregnosticon tests. The following is a brief account of the ectopic pregnancy: a 40 year old para I, gravida I missed one menstrual cycle and immediately thereafter developed mild lower abdominal pain and vaginal spotting which persisted for two weeks. The hemagglutination inhibition tube test was negative on the day following admission. The radioreceptorassay on the second day was positive. On the third day, currettage revealed no evidence of pregnancy; cul-de-sac puncture was negative, laparoscopy demonstrated an unruptured left ectopic which was removed at subsequent laparotomy.

Thirteen patients was admitted to the hospital because of suspected ectopic pregnancy. The last menstrual period ranged from 23–76 days prior to admission. Lower abdominal pain, amenorrhea, frequent vaginal staining, and an adnexal mass were the usual findings. Plasma samples were obtained from each patient prior to surgery and in one instance on four separate days for the radioreceptorassay of HCG. Conventional hem- or latex agglutination tests were performed on urine samples at the same time. The results of pregnancy tests and pathological findings are presented in Table III.

TABLE III

COMPARISON OF PREGNANCY TESTS AND PATHOLOGICAL FINDINGS IN THIRTEEN SUSPECTED ECTOPIC PREGNANCIES

| Radioreceptor-Assay | Agglutination Test | Pathology Tubal Ectopic | Days Past Last Menses |
|---|---|---|---|
| | (Number of Patients) | | |
| 7 positive | 7 negative | 7 positive | 21,23,24,36 41,51,76 |
| 3 positive | 3 positive | 3 positive | 29,61,65 |
| 1 negative | 1 positive | 1 negative | Unknown |
| 2 negative | 2 negative | 2 negative | 30,48 |

Table III indicates the results obtained by the radioreceptorassay and hemagglutination test in 13 suspected ectopic pregnancies, and in addition, the time from the last menses and the tubal histological findings. Seven of the 10 ectopic pregnancies had a positive radioreceptorassay and negative hemagglutination pregnancy test. One false positive hemagglutination test and no false positive radioreceptorassays were obtained. There was a wide range for the duration of pregnancy spanning between 23 and 76 days past the last missed period.

Figure 2:
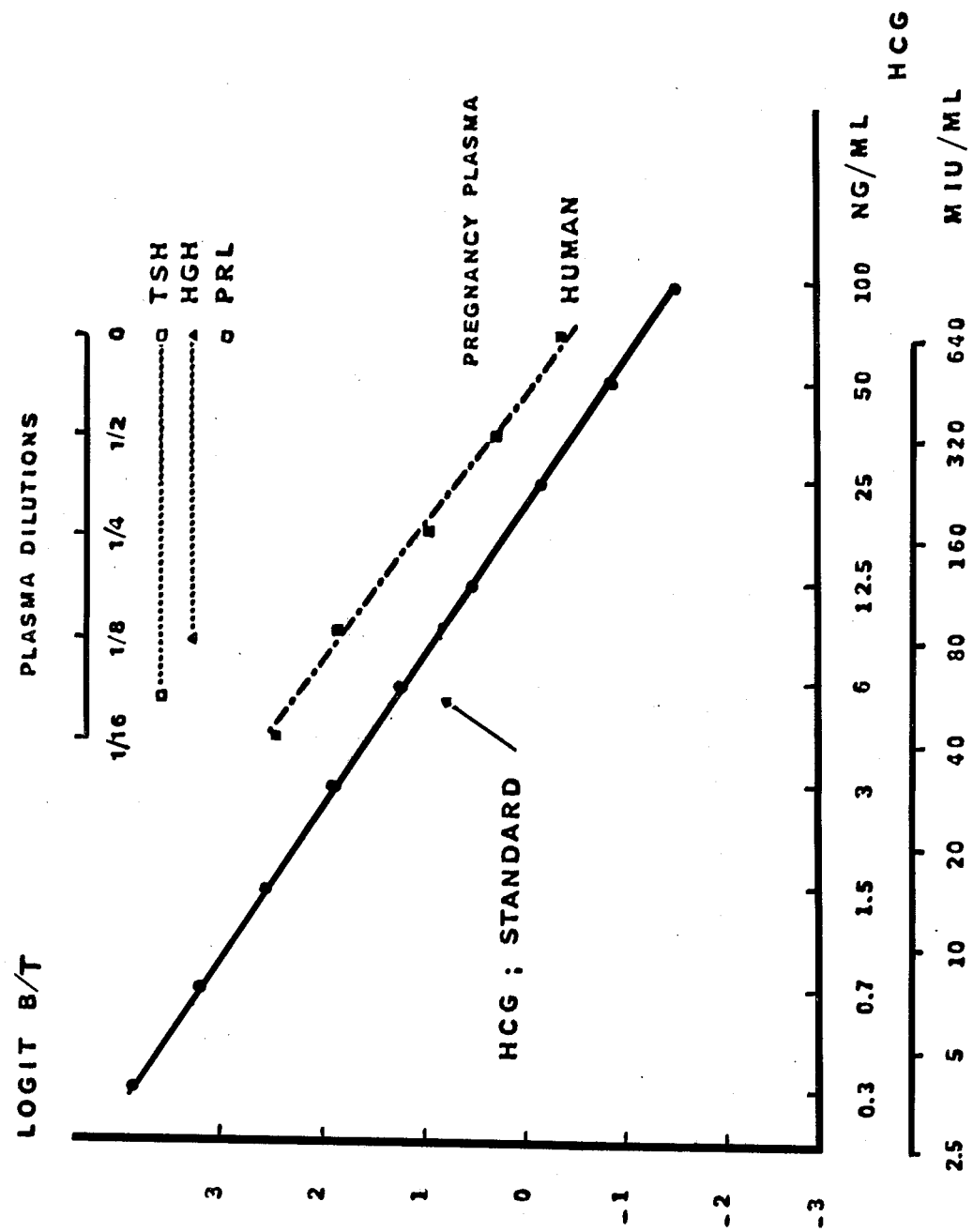
FIG. 2 illustrates the computer output of logit-log transformation of the standard for the radioreceptorassay of HCG.

The logit-log transformation of standard HCG dose-responsive curve yield a sensitivity of 0.3 ng or 3 mI-U/HCG/ml (FIG. 2). In this figure, TSH is the legend for plasma from hypothyroid patients; HGH, plasma from acromegalic subjects; PRL, plasma from women with postpartum lactation. mIU of 2nd International Reference Preparation equivalent to corresponding ng of HCG are indicated on the ordinate. Various dilutions of the plasma sample from a pregnant woman yielded a slope parallel to that of HCG indicating the validity of the assay. There was no cross-reaction with FSH, TSH, HGH, and HPRL in the assay. There was a 98–102% recovery of HCG added to the plasma samples of known hormonal concentration. The intra- and inter-assay variation in the estimates of hormonal levels of plasma pools was 6% and 11%, respectively. The radioreceptorassay, however, did not discriminate between LH and HCG. This drawback was circumvented by the observations (1) that neither LH nor FSH rise during early pregnancy as determined by specific $\beta$ subunit radioimmunoassay of FSH, LH, and HCG in the blood, (2) that the standards contain the same amount of plasma obtained from non-pregnant women during luteal phase containing low levels of LH, (3) that all unknown samples are compared with a pool of plasma from non-pregnant and various dilutions of a pool of plasma from pregnant women analyzed routinely with each assay for accuracy and quality control, and (4) finally, that during early pregnancy the HCG-LH levels are 2–3 fold higher than basal LH levels in non-pregnant women during the luteal phase.

Figure 3:
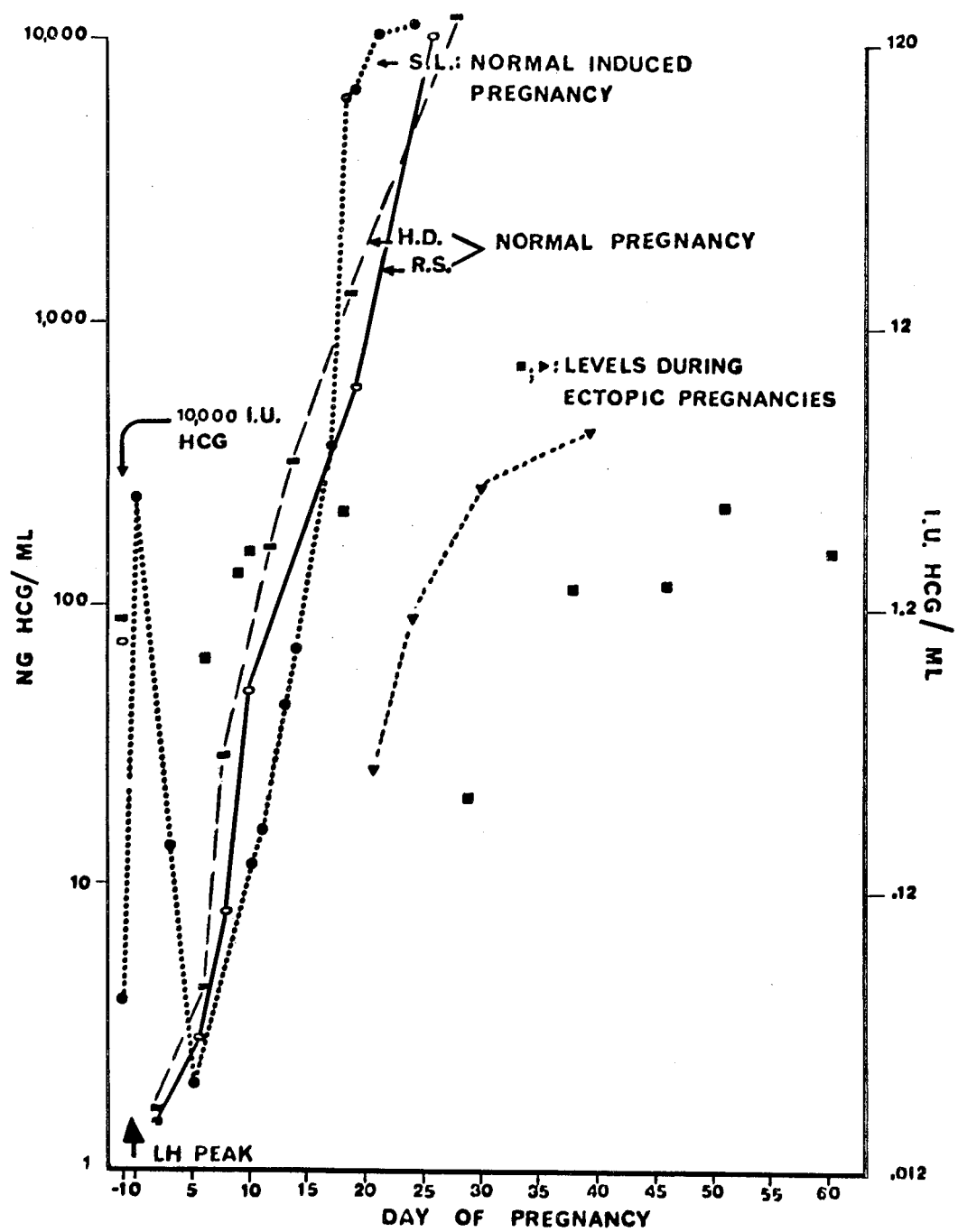
FIG. 3 is a comparison of the plasma levels of HCG during two normal (HD, RS) and one induced normal intrauterine pregnancy in S.L. with HCG levels in 10 patients with ectopic pregnancy.
Figure 3A:
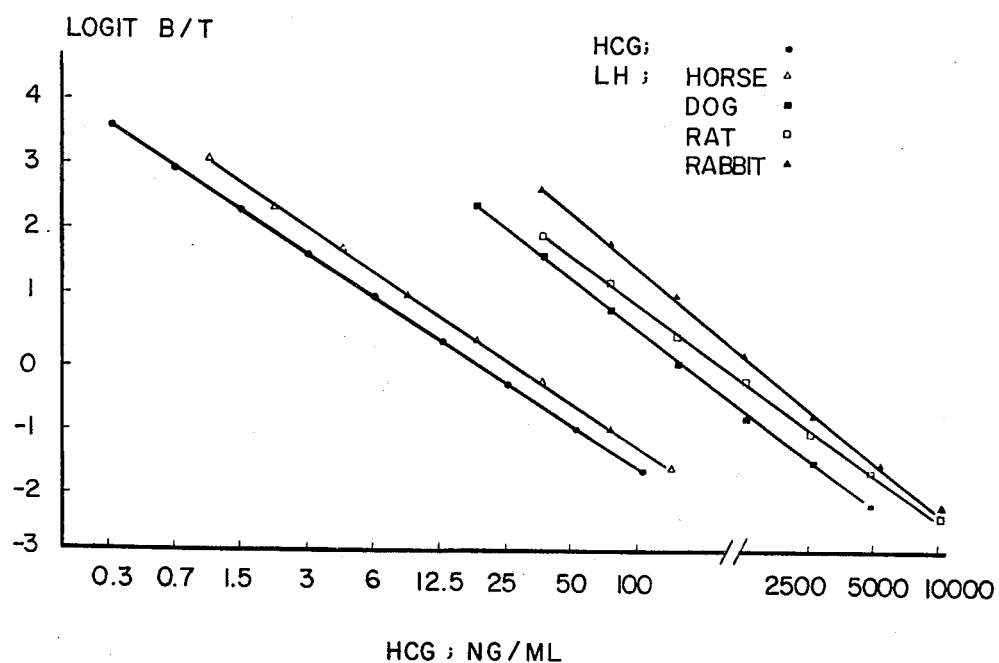
FIG. 3a is a logit-log linearization of the competitive inhibition response of the radioreceptorassay of HCG and also of LH taken from several animal species, all in the same system.

In FIG. 3, the HCG levels in 10 ectopic pregnancies are compared with normal intrauterine gravity in 2 subjects (H.D., R.S.) and 1 induced ovulation and pregnancy (S.L.) with 10,000 IU of HCG which was monitored with radioreceptorassay. The plasma levels of HCG during early induced or natural pregnancy were similar. The day of pregnancy was based on the last menstrual period reported by the patients. In one of the 10 patients (▲....▲), the radioreceptorassay was performed on days 21, 24, 30, and 42 of pregnancy. The positive radioreceptorassays on days 21 and 24 were associated with negative Pregnosticon tests. The onset of the HCG rise following LH peak was first detected in the blood samples obtained first on day 6–8 following ovulation and it might be earlier following fertilization. Three of the ectopics has assays performed prior to the first missed menses and the levels of HCG in 4 were in the range of the normal pregnancy. The other 6 octopic HCG levels were lower than the normal. These observations suggested that the early nidations in the tube, before rupture and hemorrhage, could secrete normal quantities of HCG. Later, however, when hemorrhage, increased separation and reduced blood supply occurred, the HCG secretion leveled off.

As shown in FIG. 3, in the present series of 13 suspected ectopic pregnancies, the HCG was 22 and 35 ng/ml or 0.26 and 0.42 IU, respectively, in two of the 13 cases. The detection of HCG at these low levels aided in the correct management of the patient at an earlier stage. The remaining patients had values of >100 ng/ml. The levels of HCG on days 21, 24, 30, and 42 of pregnancy (FIG. 3) were obtained from the same patient. The initial test was associated with a negative Pregnosticon* test; whereas both tests were positive on three subsequent determinations. On the 64th day, abdominal intervention was required because of a ruptured right ectopic pregnancy.

SUMMARY

The radioreceptorassay of HCG with a sensitivity of 50 pg or 3 mIU/ml plasma has provided close to 100% reliability to detect pregnancy following the first missed cycle. This test performed within 1 hour is ideally suited for clinical detection of ectopic pregnancy especially in patients who require immediate surgical intervention. Thirteen patients with suspected ectopic pregnancy were evaluated by the radioreceptorassay, one of which was followed with four separate determinations. The results of the assay were subsequently compared with those of hemagglutination pregnancy tests, clinical symptoms, and pathological findings. All the patients were diagnosed accurately by the radioreceptorassay, even when hemagglutination tests yielded false indication of pregnancy. The HCG levels during ectopic pregnancies by this assay are generally lower then those during a normal intrauterine pregnancy; in addition, much earlier (prior to the rupture) detection of pregnancy is possible than by hemagglutination tests. Furthermore, ectopic pregnancy may be excluded in patients admitted to the hospital with acute abdominal emergencies.

What is claimed is:

1. In a method for the determination of human chorionic gonadotropin (HCG), luteinizing hormone (LH) or HCG-like material in an aqueous sample involving the steps of contacting said sample with an agent capable of selectively binding said hormone, providing a means for indicating whether said binding has taken place and observing said indicating means to determine the presence of said hormone in the sample, the improvement which comprises said agent capable of selectively binding said hormone being a plasma membrane extract from the corpus luteum of a species possessing the receptor for human chorionic gonadotropin.

2. The method as defined by claim 1, wherein said receptor is obtained by a method comprising the steps of preparing a finely, comminuted tissue homogenate from corpus luteum tissue, separating the plasma membranes from said homogenate and selecting the plasma membrane fraction capable of selectively binding biologically active human chorionic gonadotropin.

3. The method as defined by claim 1, wherein said receptor is derived from a pregnant female.

4. The method as defined by claim 3, wherein said female is in the first trimester of pregnancy.

5. The method as defined by claim 1, wherein said sample is a body fluid of a female mammal and whereby the results of said method provide a determination of the condition of pregnancy.

6. The method as defined by claim 5, wherein said body fluid is selected from blood or urine.

7. The method as defined by claim 1, wherein said receptor is obtained from the corpus luteum of a mammal.

8. The method as defined by claim 7, wherein said mammal is selected from the group consisting of a cow, a sheep, a pig, and a horse.

9. The method as defined by claim 8, wherein said receptor is obtained from the corpus luteum of a cow.

10. The method as defined by claim 1, wherein said indicating means comprises a radioassay measuring means.

11. The method as defined by claim 10, wherein said radioassay measuring means comprises radioisotopically labeled human chorionic gonadotropin.

12. The method as defined by claim 11, wherein said steps of providing and observing said indicating means comprise contacting said receptor and said sample in the presence of radioisotopically labeled human chorionic gonadotropin whereby part of said labeled hormone and part of said unlabeled hormone present in the sample are bound to said receptor, separating said receptor-bound hormones from unbound hormones in said aqueous sample and measuring the radioactivity of at least said separated receptor or said aqueous sample to determine the concentration of said hormone as a function of the measured radioactivity.

13. The method as defined by claim 12, wherein said radioisotopically labeled hormone is labeled with an isotope from the group consisting of $^{125}I$, $^{131}I$, $^3H$ and $^{14}C$.

14. The method as defined by claim 13, wherein said isotope is $^{125}I$.

15. The method as defined by claim 12, wherein said sample is a body fluid of a human female suspected of being pregnant and whereby the results of said method provide a determination of the condition of pregnancy.

16. The method as defined by claim 15, whereby said body fluid is selected from blood serum or urine.

17. The method as defined by claim 16, wherein said body fluid is blood serum.

18. The method as defined by claim 17, wherein said blood serum is utilized in an amount of about 0.1 ml.

19. A reagent for receptor-chemical determination of the hormone human chorionic gonadotropin, comprising in substantially pure form the specific fraction of plasma membrane extract from the corpus luteum of a species having the receptor for the hormone human chorionic gonadotropin, said fraction being capable of selectively binding biologically active human chorionic gonadotropin.

20. A method for the preparation of a reagent for receptor-chemical determination of the hormone human chorionic gonadotropin, comprising the steps of preparing a finely comminuted tissue homogenate from corpus luteum tissue of a species having the receptor for human chorionic gonadotropin, separating the plasma membranes from said homogenate and selecting the plasma membrane fraction capable of selectively binding biologically active human chorionic goadotropin.

21. A method for determining the hormone prolactin (PRL) in an aqueous sample, comprising contacting said sample with an agent capable of selectively binding said hormone, said agent being a plasma membrane extract from the corpus luteum of a species possessing the receptor for prolactin, providing a means for indicating whether said binding has taken place and observing said indicating means to determine the presence of said hormone in the sample.

22. The method as defined by claim 21, wherein said receptor is obtained from the corpus luteum of a mammal selected from the group consisting of a cow, a sheep, a pig, and a horse.

23. The method as defined by claim 21, wherein said receptor is obtained by a method comprising the steps of preparing a finely commuinited tissue homogenate from corpus luteum tissue, separating the plasma membranes from said homogenate and selecting the plasma membrane fraction capable of selectively binding biologically active PRL.

24. The method as defined by claim 23, wherein said receptor is derived from a pregnant female in the first trimester of pregnancy.

25. The method as defined by claim 21, wherein said indicating means comprises a radioassay measuring means.

26. The method as defined by claim 25, wherein said radioassay measuring means comprises radioisotopically labeled prolactin.

27. The method as defined by claim 26, wherein said steps of providing and observing said indicating means comprise contacting said receptor and said sample in the presence of radioisotopically labeled prolactin whereby part of said labeled hormone and part of said unlabeled hormone present in the sample are bound to said receptor, separating said receptor-bound hormones from unbound hormones in said aqueous sample and measuring the radioactivity of at least said separated receptor or said aqueous sample to determine the concentration of said hormone as a function of the measured radioactivity.

28. The method as defined by claim 27, wherein said radioisotopically labeled hormone is labeled with an isotope from the group consisting of $^{125}I$, $^{131}I$, $^3H$ and $^{14}C$.

29. The method as defined by claim 28, wherein said isotope is $^{125}I$.

30. The method as defined by claim 27, wherein said sample is a body fluid of a human female suspected of being pregnant and whereby the results of said method provide a determination of the condition of pregnancy.

31. The method as defined by claim 30 wherein said body bluid is selected from blood serum or urine.

32. The method as defined by claim 31, wherein said body fluid is blood serum.

33. A method for simultaneously determining a plurality of hormones in a single aqueous sample, comprising contacting said sample with an agent capable of selectively binding each of said hormones in the sample, said agent being a plasma membrane extract from a body organ of a species which possesses in said organ the specific receptor for each of said hormones, providing a separate, distinguishable means for each hormone to be determined for indicating whether said binding has taken place and observing each of said indicating means to determine the presence of each of said hormones.

34. The method as defined by claim 33, wherein said hormones to be determined on said sample comprise human chorionic gonadotropin (HCG) and prolactin (PRL) and wherein said binding agent comprises a plasma membrane extract from the corpus luteum of a species possessing the receptor for HCG and PRL.

35. The method as defined by claim 34, wherein said receptor is obtained from the corpus luteum of an animal selected from the group consisting of a cow, a sheep, a pig and a horse.

36. The method as defined by claim 34, wherein said receptor is obtained by a method comprising the steps of preparing a finely comminuted tissue homogenate from corpus luteum tissue, separating the plasma membranes from said homogenate and selecting the plasma membrane fraction capable of selectively binding biologically active PRL and HCG.

37. The method as defined by claim 36, wherein said receptor is derived from a female in the first trimester of pregnancy.

38. The method as defined by claim 34, wherein said indicating means comprises a radioassay measuring means.

39. The method as defined by claim 38, wherein said measuring means comprises radioisotopically labeled HCG and a differently radiosotropically labeled PRL, the isotopes for labeling HCG and PRL being different.

40. The method as defined by claim 39, wherein said steps of providing and observing said indicating means comprise contacting said receptor and said sample in the presence of said radioisotopically labeled HCG and said radioisotopically labeled PRL, whereby a part of each of said labeled hormones and part of said unlabeled hormone present in the sample are bound to said receptor, separating said receptor-bound hormones from unbound hormones in said aqueous sample and measuring the radioactivity for each of said isotopes of at least said separated receptor or said aqueous sample to determine the concentration of each of said hormones as a function of the measured radioactivity.

41. The method as defined by claim 40, wherein said radioisotopically labeled HCG and PRL are labeled with two different isotopes of iodine.

42. The method as defined by claim 41, wherein said isotopes are $^{125}I$ and $^{131}I$.

43. The method as defined by claim 42, wherein said sample is a body fluid of a human female.

44. The method as defined by claim 43, wherein said fluid is blood serum of urine.

* * * * *